(12) United States Patent
del Soldato et al.

(10) Patent No.: US 7,723,382 B2
(45) Date of Patent: May 25, 2010

(54) PROCESS FOR PREPARING NITROOXYALKYL SUBSTITUTED ESTERS OF CARBOXYLIC ACIDS, INTERMEDIATES USEFUL IN SAID PROCESS AND PREPARATION THEREOF

(75) Inventors: Piero del Soldato, Monza (IT); Giancarlo Santus, Milan (IT); Francesca Benedini, Milan (IT)

(73) Assignee: Nicox S.A., Sophia Antipolis - Valbonne (FR)

( * ) Notice: Subject to any disclaimer, the term of this patent is extended or adjusted under 35 U.S.C. 154(b) by 54 days.

(21) Appl. No.: 10/522,986

(22) PCT Filed: Aug. 6, 2003

(86) PCT No.: PCT/EP03/08700

§ 371 (c)(1), (2), (4) Date: Sep. 13, 2006

(87) PCT Pub. No.: WO2004/020385

PCT Pub. Date: Mar. 11, 2004

(65) Prior Publication Data

US 2007/0112194 A1    May 17, 2007

(30) Foreign Application Priority Data

Aug. 29, 2002   (IT) .......................... MI2002A1861

(51) Int. Cl.
A61K 31/21 (2006.01)
A61K 31/40 (2006.01)
C07C 203/04 (2006.01)
C07C 69/00 (2006.01)

(52) U.S. Cl. ..................... 514/509; 514/413; 514/418; 558/480; 558/482; 560/129; 534/660

(58) Field of Classification Search .................. 514/509, 514/413, 418; 558/480, 482; 560/129; 534/660
See application file for complete search history.

(56) References Cited

U.S. PATENT DOCUMENTS

| 5,700,947 | A | * | 12/1997 | Soldato ...................... | 548/491 |
| 5,780,495 | A | * | 7/1998 | Del Soldato ................ | 514/413 |
| 5,861,426 | A | * | 1/1999 | Del Soldato et al. ........ | 514/413 |
| 6,040,341 | A | * | 3/2000 | Del Soldato et al. ........ | 514/509 |
| 6,700,011 | B1 | * | 3/2004 | Benedini et al. ............ | 558/482 |
| 7,186,753 | B1 | * | 3/2007 | Del Soldato ................ | 514/509 |
| 7,199,141 | B2 | * | 4/2007 | Del Soldato et al. ........ | 514/357 |
| 7,199,258 | B2 | * | 4/2007 | Del Soldato et al. ........ | 558/482 |
| 7,399,878 | B2 | * | 7/2008 | Del Soldato ................ | 558/482 |
| 2003/0220468 | A1 | * | 11/2003 | Lai et al. .................... | 530/331 |
| 2004/0072899 | A1 | * | 4/2004 | Letts et al. .................. | 514/509 |
| 2004/0171682 | A1 | * | 9/2004 | Del Soldato et al. ........ | 514/509 |
| 2005/0101661 | A1 | * | 5/2005 | Soldato et al. .............. | 514/456 |
| 2005/0222243 | A1 | * | 10/2005 | Earl et al. ................... | 514/419 |
| 2005/0234123 | A1 | * | 10/2005 | Belli et al. .................. | 514/509 |
| 2006/0173005 | A1 | * | 8/2006 | Del Soldato et al. ...... | 514/237.5 |

FOREIGN PATENT DOCUMENTS

| WO |    WO 95/09831 A1 |    4/1995 |
| WO |    WO 95/30641 A  |   11/1995 |
| WO |    WO 98/07701 A  |    2/1998 |
| WO |    WO 9807701 A1 * |    2/1998 |
| WO |    WO 01/10814 A1 |    2/2001 |
| WO | WO 02092072 A 2 * |   11/2002 |
| WO | WO 03000643 A 1 * |    1/2003 |

OTHER PUBLICATIONS

Kawashima et al. J.Med.Chem. 1993, 36, 815-819.*
Ogawa et al. PharmBull Japan Jun. 1993 1049-54.*
Database Online-Chemical Abstracts Service; Movsumzade, et al.; "Effect of Bromine Nitrate on Olefin-Oxirane Mixtures"; 1975.
Database Online-Chemical Abstract Service; McKillop, et al.; "Mercury-Assisted Solvolyses of Alkyl Halides. Simple Procedures for the Preparation of Nitrate Esters Acetate Esters, Alcohols, and Ethers"; 1974.
Chemical and Pharmaceutical Bulletin; Ogawa, et al.; "Synthesis and Antihypertensive Activites of New 1,4-Dihydropyridine Derivatives Containing Nitrooxyalkylester Moieties at the 3-And 5-Positions"; vol. 41; No. 6; pp. 1049-1054; Jun. 1993.
Journal of Medicinal Chemistry, American Chemical Society; Kawashima; "Synthesis and Pharmacological Evaluation of (Nitrooxy)alkyl Apovincaminates"; vol. 36, pp. 815-819; 1993.
T. Ogawa et al., "Synthesis and Configurational Assignment of Methyl 3-Nitrooxypropyl 1,4-Dihydro-2,6-dimethyl-4-(3-nitrophenyl)pyridine-3,5-dicarboxylate", *J. Chem. Soc. Perkin Trans*. pp. 525-528, 1993.

* cited by examiner

*Primary Examiner*—Karl Puttlitz
*Assistant Examiner*—Yate' K Cutliff
(74) *Attorney, Agent, or Firm*—Arent Fox LLP

(57) ABSTRACT

The present invention refers to a process for preparing a compound of general formula (A), as reported in the description, wherein R is a radical of a drug and R1-R12 are hydrogen or alkyl groups, m, n, o, q, r and s are each independently an integer from 0 to 6, and p is 0 or 1, and X is O, S, SO, SO2, NR13 or PR13 or an aryl, heteroaryl group, said process comprising reacting a compound of formula (B) R—COOZ (B) wherein R is as defined above and Z is hydrogen or a cation selected from: Li+, Na+, K+, Ca++, Mg++, tetralkylammonium, tetralkylphosphonium, with a compound of formula (C), as reported in the description, wherein R1-R12 and m, n, o, p, q, r, s are as defined above and Y is a suitable leaving group.

12 Claims, No Drawings

PROCESS FOR PREPARING NITROOXYALKYL SUBSTITUTED ESTERS OF CARBOXYLIC ACIDS, INTERMEDIATES USEFUL IN SAID PROCESS AND PREPARATION THEREOF

CROSS-REFERENCE TO RELATED APPLICATION

This application is a National Stage entry of International Application No. PCT/EP2003/008700, filed Aug. 6, 2003, the entire specification and claims of which are incorporated herewith by reference.

The present invention relates to a process for preparing nitrooxyalkyl substituted esters of carboxylic acids, to intermediates useful in said process and to their preparation.

Many carboxylic acid nitrooxyalkyl esters are pharmacologically active products. For example, 1,4-dihydropyridine derivatives having nitrooxy moieties at the C-3 and/or C-5 ester position have shown to be active calcium-channel blockers similar to nifedipine and nicardipine (J. Chem. Soc. Perkin Trans I, 525 (1993)). In literature, several methods for synthesizing nitrooxyalkyl esters are reported. In this way, the nitrooxy moiety may be for example introduced by nucleophilic substitution of a leaving group already present on the alkyl chain of alkyl ester precursor. In particular, 2-(6-methoxy-2-naphtyl)-propionic acid 4-nitrooxybutyl ester has been synthesized reacting 4-chlorobutyl 2-(6-methoxy-2-naphtyl)-propionate with silver nitrate (WO 95/09831), whereas 2-(benzoylphenyl)propionic acid 4-nitrooxybutyl ester (ketoprofen nitrooxybutyl ester) has been prepared reacting the 2-(3-benzoylphenyl)propionic acid sodium salt with 1,4-dibromobutane to give the corresponding bromobutyl ester, which was then treated with silver nitrate to yield the desired nitrooxy derivative. Both processes have the disadvantage that during the introduction of nitrooxy group, impurities of difficult removal are often obtained, such as silver salts (AgCl, AgBr) and silver metal, this being prejudicial to the use of the end-products in therapeutic field, in which an improved purity is always requested.

A further known process for preparing the above mentioned nitrooxyalkyl esters is the insertion of nitrooxyalkyl group by reacting the carboxylic acid or a derivative thereof (halide) with a nitrooxyalkyl alcohol or with a nitrooxyalkyl bromide. For example, 2-(S)-(6-methoxy-2-naphtyl)-propionic acid 4-nitrooxybutyl ester is prepared treating the corresponding acid chloride with 4-nitrooxybutan-1-ol in methylene chloride and in presence of potassium carbonate (WO 01/10814). This method has also the disadvantage that several by-products are formed, being in fact very difficult to obtain nitrooxyalkyl alcohols and the acyl halide in a pure form; moreover, for example 4-nitrooxybutan-1-ol is stable only in solution and it cannot be isolated as a pure substance.

It was thus an object of the present invention to provide a new process for preparing carboxylic acid nitrooxyalkyl esters not having the above mentioned disadvantages and wherein impurities and by-products are present in an essentially negligible amount.

The present invention relates to a process for preparing a compound of general formula (A)

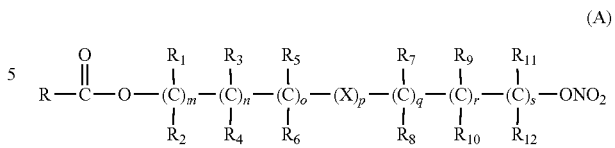

wherein $R_1$-$R_{12}$ are the same or different and independently are hydrogen, straight or branched $C_1$-$C_6$ alkyl, optionally substituted with aryl;

m, n, o, q, r and s are each independently an integer from 0 to 6, and p is 0 or 1, and X is O, S, SO, $SO_2$, $NR_{13}$ or $PR_{13}$, in which $R_{13}$ is hydrogen, $C_1$-$C_6$ alkyl, or X is selected from the group consisting of:

saturated or unsaturated $C_5$-$C_7$ cycloalkylene, optionally substituted with one or more straight or branched $C_1$-$C_3$ alkyl groups;

arylene, optionally substituted with one or more halogen atoms, straight or branched alkyl groups containing from 1 to 4 carbon atoms, or a straight or branched $C_1$-$C_3$ perfluoroalkyl;

a 5 or 6 member saturated, unsaturated, or aromatic heterocyclic ring selected from

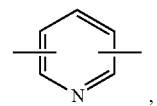

(X1)

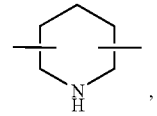

(X2)

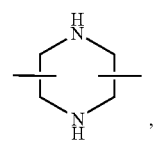

(X3)

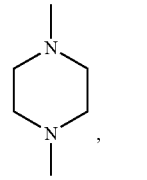

(X4)

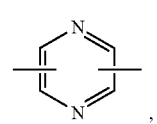

(X5)

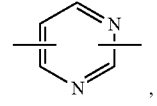

(X6)

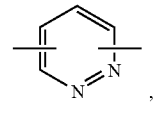

(X7)

-continued

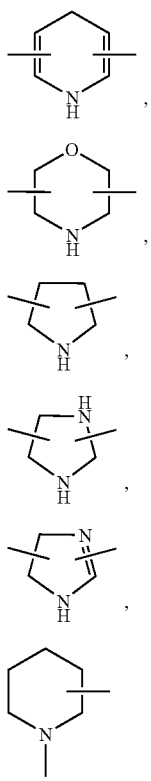

(X8)

(X9)

(X10)

(X11)

(X12)

(X13)

wherein the bonds, when they have an undefined position, are intended to be in any possible position in the ring;
R is selected from:

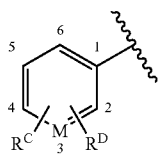

(I)

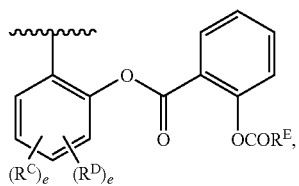

(II)

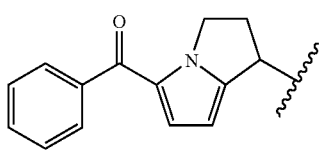

(III)

wherein M is a carbon or nitrogen atom;
$R^C$ is selected from: H, OH, $NH_2$, $R^E CONH-$, $R^E COO-$, an heterocyclic residue with 5 or 6 atoms that may be aromatic, saturated or unsaturated, containing one or more heteroatoms selected from oxygen, nitrogen or sulfur, and phenylamino (PhNH—), in which the aromatic ring may be substituted with one or more substituents selected from the group consisting of halogen, preferably chlorine or fluorine, straight or branched $C_1$-$C_4$-alkyl, for example methyl, straight or if possible branched perfluoroalkyl, for example trifluoromethyl;

$R^E$ is selected from the group consisting of straight or branched $C_1$-$C_5$-alkyl, phenyl substituted with $OCOR^F$, wherein $R^F$ is selected from the group consisting of methyl, ethyl or straight or branched $C_3$-$C_6$-alkyl or phenyl;

$R^D$ is selected from: H, OH, halogen, $-NH_2$, straight or branched $C_1$-$C_6$-alkoxy, perfluoroalkyl having from 1 to 4 carbon atoms, for example $-CF_3$, mono o di-($C_1$-$C_6$)alkylamino; with the proviso that $R^C$ and $R^D$ can not be both H;

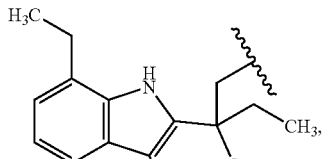

(IV)

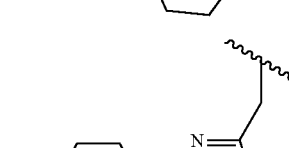

(V)

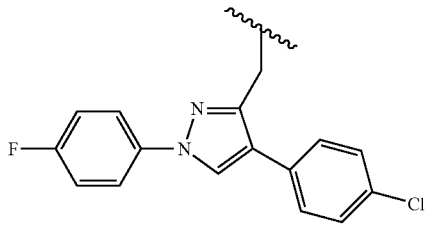

(VI)

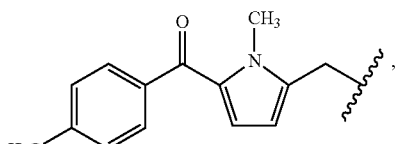

(VII)

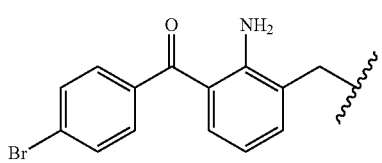

(VIII)

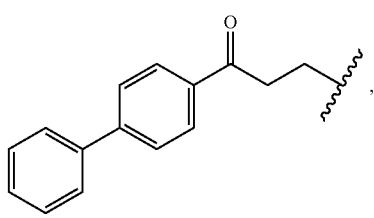

(IX)

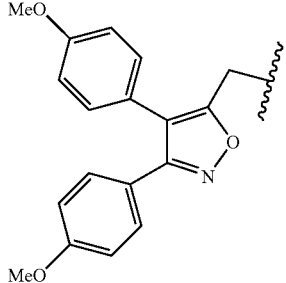

-continued
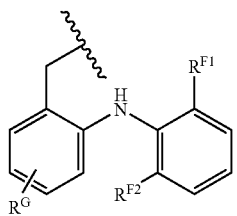
(X)
wherein $R^{F1}$ and $R^{F2}$ are halogens selected from chlorine, fluorine or bromine, $R^G$ is hydrogen, straight or branched $C_1$-$C_6$-alkyl, preferably methyl;
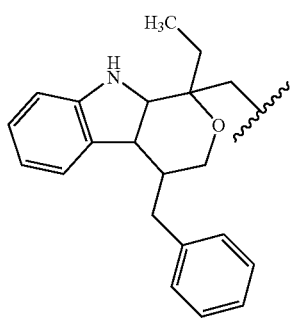
(XI)
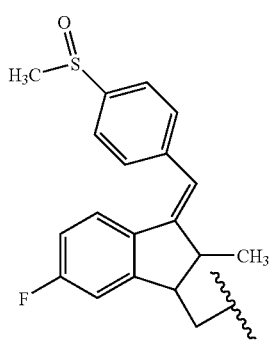
(XII)
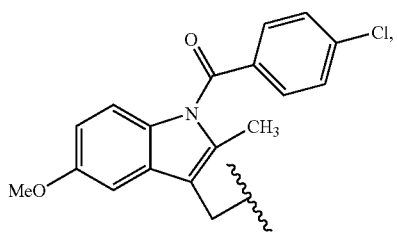
(XIII)
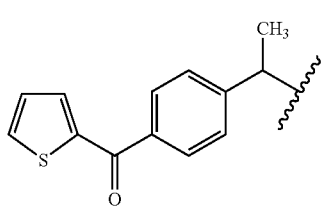
(XIV)
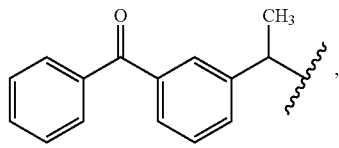
(XV)
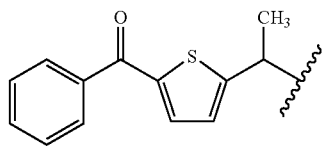
(XVI)
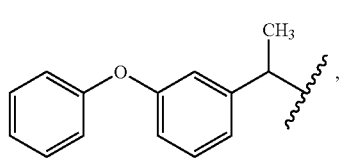
(XVII)
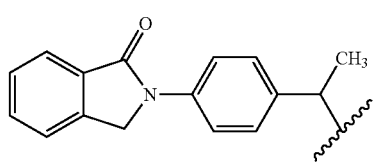
(XVIII)
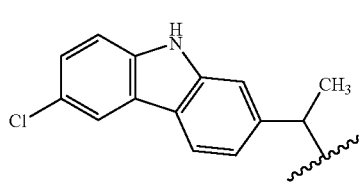
(XIX)
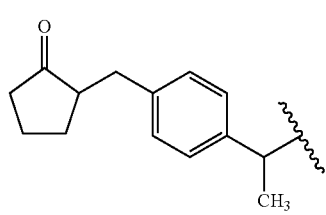
(XXI)
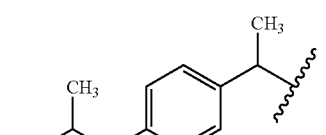
(XXII)
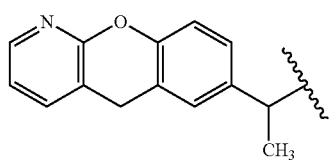
(XXIII)
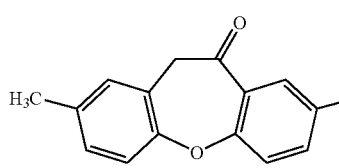
(XXIV)

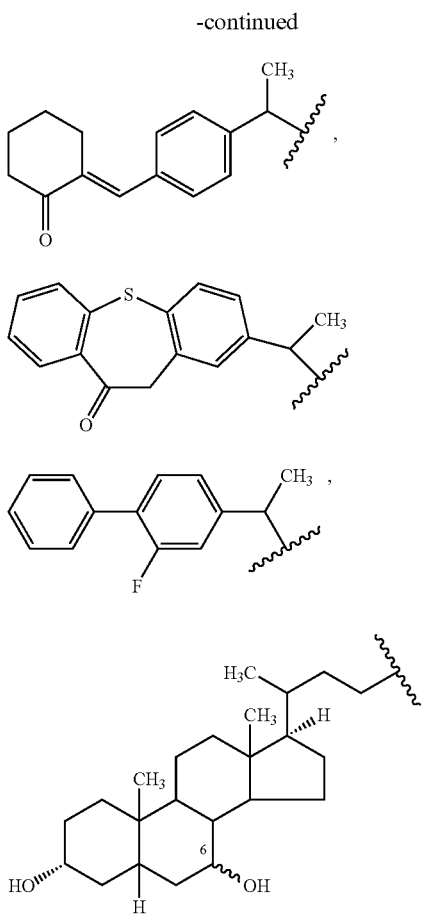

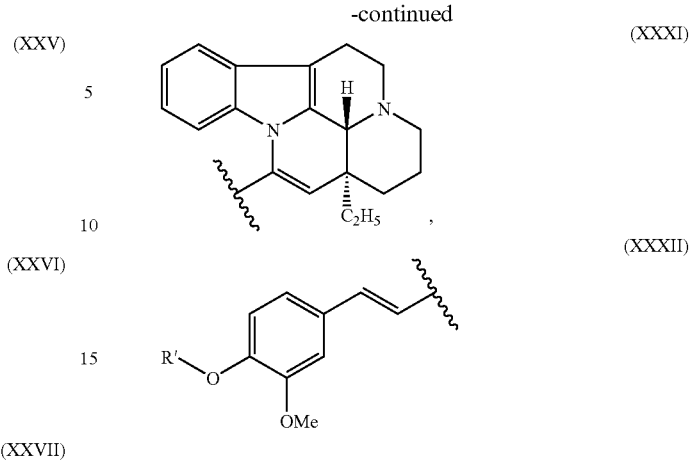

wherein the bond at 6 position in formula (XXVIII) may be α or β;

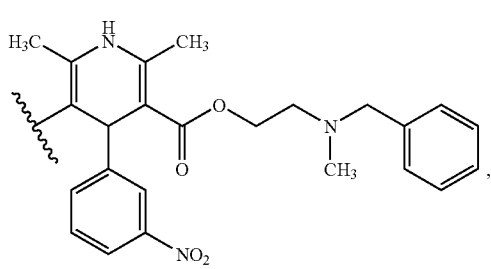

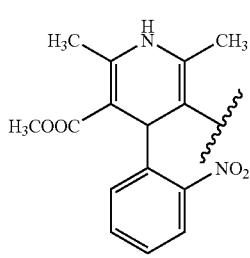

wherein R' in formula (XXXII) is H or R(CO)—, in which R is selected from the radicals represented by formulae (I)-(XXXI);

in all the formulae (I-XXXII) listed above, the wavy line represents always the position wherein —COO— group is bound;

said process comprising reacting a compound of formula (B)

$$R-COOZ \tag{B}$$

wherein R is as above defined and Z is hydrogen or a cation selected from: Li+, Na+, K+, Ca++, Mg++, trialkylammonium tetralkylammonium, tetralkylphosphonium, with a compound of the following formula (C)

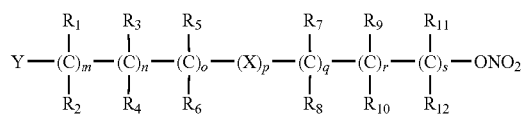

wherein $R_1$-$R_{12}$ and m, n, o, p, q, r, s are as defined above and Y is selected from an halogen atom such as Br, Cl, I;

—$BF_4$, —$SbF_6$, $FSO_3$—, $R_4SO_3$—, in which $R_4$ is a straight or branched $C_1$-$C_6$ alkyl, optionally substituted with one or more halogen atoms, or a C1-C6 alkylaryl;

$R_B COO^-$, wherein $R_B$ is straight or branched $C_1$-$C_6$ alkyl, aryl, optionally substituted with one or more halogen atoms or $NO_2$ groups, $C_4$-$C_{10}$ heteroaryl and containing one or more heteroatoms, which are the same or different, selected from nitrogen, oxygen sulfur or phosphorus;

aryloxy optionally substituted with one or more halogen atoms or $NO_2$ groups, or heteroaryloxy.

In particular when in formula (A) the R residue is as defined by formula (I), wherein M is a carbon atom, $R^C$=$R^E$COO— in 2 position, in which $R^E$ is $CH_3$ and $R^D$=H, the compound is known as acetylsalicylic acid;

when in formula (A) the R residue is represented by formula (I), wherein M is a carbon atom, $R^C$=$NH_2$ in 5 position, $R^D$=OH in 2 position, the compound is known as mesalamine;

when in formula (A) the R residue is represented by formula (I), in which M is a carbon atom, $R^C$=PhNH— in 2 position, wherein Ph- is the 3-trifluoromethylbenzene radical, $R^D$=H, the compound is known as flufenamic acid;

when in formula (A) the R residue is represented by formula (I), in which M is a carbon atom, $R^C$=PhNH— in 2 position, wherein Ph is the 2,6-dichloro-3-methyl-benzene moiety, and $R^D$=H, the compound is known as meclofenamic acid;

when in formula (A) the R residue is represented by formula (I), in which M is a carbon atom, $R^C$=PhNH— in 2 position, wherein Ph è the 2,3-dimethylbenzene radical, and $R^D$=H, the compound is known as mefenamic acid;

when in formula (A) the R residue is defined by formula (I), in which M is a carbon atom, $R^C$=PhNH— in 2 position, wherein Ph is a 2-methyl-3-chlorobenzene group, and $R^D$=H, the compound is known as tolfenamic acid;

when in formula (A) the R residue is represented by formula (I), in which M is a nitrogen atom, $R^C$=PhNH— in 2 position, wherein Ph is the 2-trifluoromethylbenzene radical, and $R^D$=H, the compound is known as niflumic acid;

when in formula (A) the R residue is represented by formula (I), in which M is a nitrogen atom, $R^C$=PhNH— in 2 position, wherein Ph is the 2-methyl-3-trifluoromethyl-benzene radical, and $R^D$=H, the compound is known as flunixin;

when in formula (A) the R residue is represented by formula (II), in which e=0 and $R^E$ is a methyl group, the compound is known as acetylsalicylsalicylic acid;

when in formula (A) the R residue is defined by formula (III), the compound is known as Ketorolac;

when in formula (A) the R residue is represented by formula (IV), the compound is known as etodolac;

when in formula (A) the R residue is represented by formula (V), the compound is known as pirazolac;

when in formula (A) the R residue is defined by formula (VI), the compound is known as tolmetin;

when in formula (A) the R residue is defined by formula (VII), the compound is known as bromfenac;

when in formula (A) the R residue is represented by formula (VIII), the compound is known as fenbufen;

when in formula (A) the R residue is represented by formula (IX), the compound is known as è mofezolac;

when in formula (A) the R residue is represented by formula (X), wherein $R^{F1}$ and $R^{F2}$ are Cl and $R^G$ is hydrogen, the compound is known as diclofenac;

when in formula (A) the R residue is defined by formula (X), wherein $R^{F2}$ is chlorine, $R^{F1}$ is fluorine and $R^G$ is a methyl group, the compound is known as COX-189;

when in formula (A) the R residue is represented by formula (XI), the compound is known as pemedolac;

when in formula (A) the R residue is defined by formula (XII), the compound is known as sulindac;

when in formula (A) the R residue is defined by formula (XIII), the compound is known as indomethacin;

when in formula (A) the R residue is represented by formula (XIV), the compound is known as suprofen;

when in formula (A) the R residue is represented by formula (XV), the compound is known as ketoprofen;

when in formula (A) the R residue is represented by formula (XVI), the compound is known as tiaprofenic acid;

when in formula (A) the R residue is defined by formula (XVII), the compound is known as fenoprofen;

when in formula (A) the R residue is defined by formula (XVIII), the compound is known as indoprofen;

when in formula (A) the R residue is represented by formula (XIX), the compound is known as carprofen;

when in formula (A) the R residue is defined by formula (XXI), the compound is known as loxoprofen;

when in formula (A) the R residue is represented by formula (XXII), the compound is known as ibuprofen;

when in formula (A) the R residue is defined by formula (XXIII), the compound is known as pranoprefen;

when in formula (A) the R residue is defined by formula (XXIV), the compound is known as bermoprofen;

when in formula (A) the R residue is represented by formula (XXV), the compound is known as CS-670;

when in formula (A) the R residue is defined by formula (XXVI), the compound is known as zaltoprofen;

when in formula (A) the R residue is represented by formula (XXVII), the compound is known as flurbiprofen;

when in formula (A) the R residue is represented by formula (XXVIII), in which bond to the hydroxy group at 6 position is β standing, the compound is known as ursodeoxycholic acid;

when in formula (A) the R residue is represented by formula (XXVIII), wherein bond to the hydroxy group at 6 position is α standing, the compound is known as chenodeoxycholic acid;

when in formula (A) the R residue is represented by è formulae (XXIX) and (XXX), the compounds belong to the nifedipine class;

when in formula (A) the R residue is defined by formula (XXXI), the compound is known as apovincaminic acid;

when in formula (A) the R residue is represented by formula (XXXII), wherein R' is hydrogen, the compound is known as ferulic acid;

It has been surprisingly found that when in the compound of formula (B) R is the radical of formula (XXXII) wherein R' is H (ferulic acid) the reaction is highly selective towards the formation of the ester of formula (A), in spite of the fact that the presence of two nucleophilic groups in the ferulic acid (the carboxylic group and the fenolic group) could give a substantial formation of the nitroxyalkylether.

Preferably the present invention relates to a process for preparing a compound of formula (A) as above defined wherein:

the substituents $R_1$—$R_{12}$ are the same or different and independently are hydrogen or straight or branched $C_1$-$C_3$ alkyl, m, n, o, p, q, r and s are as defined above, X is O, S or

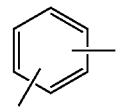

(X1)

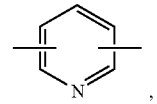

(X2)

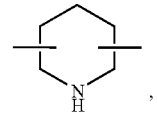

(X3)

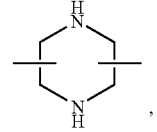

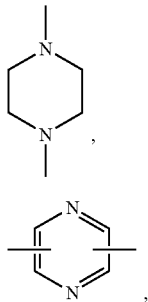

(X4)

(X5)

Most preferably the present invention relates to a process for preparing a compound of formula (A) as above defined wherein $R_1$-$R_4$ and $R_7$-$R_{10}$ are hydrogens, m, n, q, r, are 1, o and s are 0, p is 0 or 1, and X is O or S.

Preferred compounds of formula (C) as above defined are those wherein Y is selected from the group consisting of —$BF_4$, —$SbF_6$, $FSO_3$—, $CF_3SO_3$—, $C_2F_5SO_3$—, $C_3F_7SO_3$—, $C_4F_9SO_3$—, p-$CH_3C_6H_4SO_3$ —.

The reaction is carried out in an organic solvent, generally an aprotic, dipolar solvent such as acetone, tetrahyrofurane, dimethylformamide, N-methylpyrrolidone, sulfolane, acetonitrile.

Alternatively the above reported reaction is carried out in a biphasic system comprising an organic solvent selected from toluene, chlorobenzene, nitrobenzene, tert-butyl-methylether and a water solution wherein the organic solution contains (C) and the water solution contain an alkaline metal salt of (B), in presence of a phase transfer catalyst such as onium salts, for example tetralkylammonium and tetraalkylphosphonium salts.

The compounds of formula (B) and (C) are reacted at a (B)/(C) molar ratio of 2-0.5, preferably of 1.5-0.7 and at a temperature ranging from 0° C. to 100° C., preferably from 15° C. to 80° C.

The carboxylic acid salt may be prepared separately or may be generated "in situ", for example performing the reaction between (B) and (C) in the presence of a stoichiometric amount of a tertiary amine, or employing an amount in excess of said amine.

Another object of the present invention is the preparation of compounds of formula (C), by nitrating compounds of formula (D) reported here below, with a nitrating agent such as sulfonitric mixture and the like:

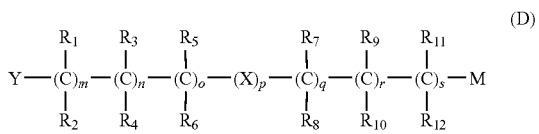

(D)

wherein M is OH, and

Y, X, m, n, o, p, q, r, s and $R_1$—$R_{12}$, have the meanings mentioned above.

Further object of the present invention is the preparation of compounds of formula (C), characterized in that a compound of the following formula (E) is reacted with nitrating agents selected for example from alkaline metal nitrates, quaternary ammonium nitrates, quaternary phosphonium salts and $AgNO_3$, $Zn(NO_3)_2 \cdot 6H_2O$;

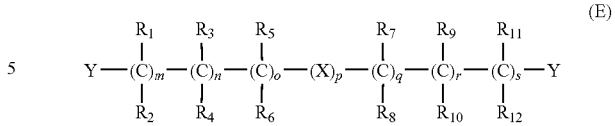

(E)

wherein:
Y, X, m, n, o, p, q, r, s and $R_1$—$R_{12}$, have the meanings mentioned above.

Another object of the present invention is the preparation of compounds of formula (C), characterized in that a compound of formula (F)

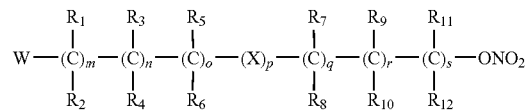

(F)

wherein W is OH or halogen is reacted with a compound selected from alkanoylsulfonylchloride, trifluoromethansulfonic acid anhydride when W is OH or $AgSbF_6$, $AgBF_4$, $AgClO_4$, $CF_3SO_3Ag$, $AgSO_3CH_3$, $CH_3C_6H_4SO_3Ag$ when W is halogen.

Nitration of compound (D) was performed in an organic solvent, generally in a solvent selected from acetone, tetrahydrofurane, dimethylformamide, N-methylpyrrolidone, sulfolane, acetonitrile, methylene chloride etc., with nitrating agents selected from transition metal salts or, when M is OH, with nitrating systems based on nitric acid, such as the sulfonitric mixture.

The (D)/nitrating agent molar ratio is of from 2 to 0.5, in particular of 1.5 to 0.5.

Nitration was performed at a temperature ranging from 0° C. to 100° C., preferably from 15° C. to 80° C.

The reaction product (C) may be isolated or its solution can be employed as such for the reaction with substrate (B) to give (A).

Nitration of compound (E) was carried out in an organic solvent, generally in a solvent selected from acetone, tetrahydrofurane, dimethylformamide, N-methylpyrrolidone, sulfolane, acetonitrile, methylene chloride etc., with nucleophilic nitrating agents such as alkaline metal nitrates, onium salt nitrates, for example tetraalkylammonium, tetraalkylphosphonium or trialkylammonium nitrate and so on.

Nitration was performed at a temperature of from 0° C. to 100° C., in particular of 15° C. to 80° C.

The molar ratio between (E) and the nitrating agent is of from 20 to 2, preferably of 8 to 1.

The reaction product (C) may be isolated or its solution can be employed such as in the reaction with substrate (B) to give (A).

The reaction for obtaining compound (C) from (F) was carried out in an organic solvent, generally selected from the group consisting of acetone, tetrahydrofurane, dimethylformamide, N-methylpyrrolidone, sulfolane, acetonitrile, methylene chloride and the like, with a reactive compound selected from transition metal salts of Y or, when W is OH, the reaction was performed with an acid chloride such as methanesulfonyl chloride etc., or with a suitable anhydride such as trifluoromethanesulfonic anhydride.

The reaction was performed at a temperature ranging from −20° C. to 100° C., in particular from −20° to 60° C.

The molar ratio between (F) and the reagent is of from 2 to 0.5, preferably of 1.5 to 0.5.

The reaction product (C) may be isolated or its solution can be employed as such in the reaction with substrate (B) to give (A).

The following examples are to further illustrate the invention without limiting it.

EXAMPLES

Preparation of 4-nitrooxybutyl bromide according to
Chem. Pharm. Bull., 1993, 41, 1040

Nitric acid (90%, 0.8 mol) was dropped under stirring in sulfuric acid maintained at 0° C. (0.8 mol) and the mixture was then stirred at 0° C. for 80 minutes. In the solution thus obtained and maintained at 0° C., under stirring 4-bromobutanol was dropped (0.4 mol) and the mixture was stirred at the same temperature for additional 210 minutes. The solution was then poured in a water-ice mixture and extracted twice with diethyl ether. The ether extracts were combined together and washed with a sodium bicarbonate saturated solution. The solvent was evaporated off under vacuum to give a yellow oil (yield: 84.8%).

Example 1

Preparation of 4-nitrooxybutyl p-toluenesulfonate

To a solution of 4-bromobutanol (5.0 g, 33 mmol) in pyridine (50 ml) kept at 0° C., under stirring and under nitrogen atmosphere tosyl chloride (6.8 g, 36 mmol) was added. The resulting solution was kept under stirring for further 20 minutes and then stored overnight at −18° C. The reaction mixture was poured in a water/ice mixture (about 400 ml) and extracted with ethyl ether (500 ml). The organic phase was washed with 6N hydrochloric acid (500 ml) and dried on sodium sulfate. After evaporation of the solvent under vacuum, an oily residue was obtained (7 g). To a solution of the oily residue (7 g) in acetonitrile (50 ml) and maintained under stirring at room temperature, silver nitrate (7.8 g, 46 mmol) was added. After nearly 15 minutes, the formation of a yellow, insoluble product was observed. The heterogeneous mixture was kept under stirring overnight. The insoluble was removed by filtration and the solution was poured in water (200 ml) and extracted with ethyl ether (2×250 ml). The combined organic extracts were dried over sodium sulfate. Evaporation of the solvent under vacuum afforded an oily residue (5 g).

Chromatography of the residue on silica gel (100 g), by hexane/ethyl ether mixture as eluent, gave the title product (3 g), m.p. 38-40° C., purity higher than 98%, determined by HPLC.

FTIR (solid KBr, cm −1): 2966, 1626, 1355, 1281, 1177, 1097, 959, 876, 815, 663, 553.

300 MHz 1H NMR (CDCl3) delta 1,77 (m, 4H); 2,35 (s, 3H); 4,06 (m, 2H); 4,38 (m, 2H); 7,36 (2H); 7,7 (2H).

Example 2A

Synthesis of (E) -3-(4-hydroxy-3-methoxyphenyl)-2-propenoic acid 4-nitrooxybutyl etser A mixture obtained pouring ferulic acid (1.94 g, 10 mmol), 4-nitrooxybutyl bromide (1.98 g, 10 mmol) and triethylamine (1.21 g, 12 mmol) in dimethylformamide (10 ml), was stirred for 3 days at 25° C. After evaporation in vacuo of DMF, an oil was obtained (2.3 g) that, according to NMR and HPLC analysis, mainly consists of unreacted ferulic acid and its 4-nitrooxybutyl ester. The ester was separated from acid by flash chromatography with a 65% yield.

Example 2B

Synthesis of (E)-3-(4-hydroxy-3-methoxyphenyl)-2-propenoic acid 4-nitrooxybutyl ester (E)-3-(4-Hydroxy-3-methoxyphenyl)-2-propenoic acid (670 mg, 3.46 mmol) and 4-(nitrooxy)butyl 4-p-toluensulfonate (1.00 g, 3.46 mmol) were dissolved in 40 ml of DMF and the solution poured in a three-necked flask kept under argon and under magnetic stirrer. Subsequently, triethylamine (0.52 ml, 3.81 mmol) was added and the mixture was allowed to react at room temperature. The course of the reaction was followed by TLC (EtOAc as the eluent) and by LC/MS ESI-using a RP-C18 4.6×100 mm column. After 72 hours the reaction conversion was ca. 40%. Additional 0.1 equivalents of tosylate were then added to the solution (100 mg, 0.346 mmol) and the mixture was reacted for other 24 hours. After this period the solution was poured in water and extracted with $Et_2O$ (3×75 ml). The combined organic phases were washed with a saturated solution of $NaHCO_3$ and water, dried over $Na_2SO_4$ and concentrated under reduced pressure.

The residue was chromatographed over silica gel (using ethyl acetate/petroleum ether 9:1 as the eluent) to provide the desired ester product in 70% yield.

The IR and LC-MS ESI-spectra of the peak product were identical to those of an authentic sample.

Analyses

TLC: (Ethyl acetate) Rf=0.60 HPLC purity: 72%. MS (ESI neg): 310 (M-H) IR(film) $cm^{-1}$: 3450 (br OH), 2964, 1707 (C=O), 1631 ($ONO_2$), 1599, 1514, 1448, 1280 ($ONO_2$).

Example 3A

Synthesis of
5-t-butoxycarbonylamino-2-hydroxyben-zoic acid 4-(nitrooxy)butyl ester The process of Example 2A was repeated, replacing however ferulic acid by 5-t-butoxycarbonylaminosalicilic acid. The title compound was obtained with a yield of 50%.

Example 3B

Synthesis of
5-t-butoxycarbonylamino-2-hydroxybenzoic acid 4-(nitrooxy)butyl ester To a mixture comprising DMF (200 ml), 5-t-butoxycarbonylaminosalicylic acid (4.37 g, 17.3 mmol) and 4-nitrooxybutyl p-toluenesulfonate (5 g, 17.3 mmol), at room temperature and under stirring triethylamine was added (2,6 ml; 19 mmol). The reaction mixture was maintained 3 days under stirring at room temperature. It was then poured in water and extracted with ethyl ether. The combined organic phases were washed with a sodium carbonate solution and then with water. After drying on sodium sulfate, the evaporation of the solvent yields a raw product that purified by silica gel chromatography gives the title compounds with a yield of 65%.

Example 4

Synthesis of potassium (E)-3-(4-hydroxy-3-methoxyphenyl)-2-propenoate

Potassium hydroxide (580 mg, 10.3 mmol) was dissolved in methanol (10 ml) and put in a three-necked flask. Stirring was set on. Subsequently, (E)-3-(4-Hydroxy-3-methoxyphenyl)-2-propenoic acid (2.00 g, 10.3 mmol) in methanol (20 mL) was added to this solution through a funnel. After the addition was ended, the solution was allowed to react at room temperature for 3 h. Methanol was then evaporated off and then yellow solid residue was washed with $Et_2O$ and dried under reduced pressure. The product was obtained as a yellowish solid (2.40 g, quantitative yield).

Analyses

IR(KBr) $cm^{-1}$: 3388, 1643, 1561 (C=O), 1524, 1404, 1263, 1204, 1152, 1121.

Example 5A

Synthesis of (E)-3-(4-hydroxy-3-methoxyphenyl)-2-propenoic acid 4-(nitrooxy)butyl ester Potassium (E)-3-(4-Hydroxy-3-methoxyphenyl)-2-propenoate (1.00 g, 4.3 mmol) was dissolved in 40 ml of DMF and poured in a three-necked flask kept under argon and magnetic stirring. The mixture was cooled at 0-5° C. through an ice bath and 4-(nitrooxy)butyl 4-p-toluensulfonate (1.25 g, 4.3 mmol) in DMF (10 ml) was added through a funnel. After the addition, the resulting mixture was stirred under argon, while the temperature was allowed to rise to r.t. (25° C.). The reaction course was followed by TLC and LC/MS ESI-. After 6 hours the conversion was complete. The solution was then poured in water and extracted with $Et_2O$ (3×75 ml). The combined organic phases were washed with a saturated solution of $NaHCO_3$ and water, dried over $Na_2SO_4$ and the volatiles removed under reduced pressure to provide a residue. The residue was washed with petroleum ether and dried under reduced pressure to provide the desire ester in 95% yield.

Analyses

HPLC purity: 95% MS (ESI neg): 310 (M-H) IR(film) $cm^{-1}$: 3450 (br OH), 2964, 1707 (C=O), 1631 ($ONO_2$), 1599, 1514, 1448, 1280 ($ONO_2$). $^1H$ NMR ($CDCl_3$, 300 MHz): □ 1.72-1.93 (4H, m, $CH_2$—$CH_2$), 3.92 (3H, s, $OCH_3$), 4.22-4.26 (2H, m, $CH_2$—COO), 4.50-4.54 (2H, m, $CH_2$—$ONO_2$), 5.95 (1H, br s, OH), 6.28 (1H, d, J=15.9 Hz, CH=), 7.03-7.10 (2H, m, aromatic H), 7.36 (1H, d, J=7.8 Hz, aromatic H), 7.61 (1H, d, J=15.9 Hz, CH=).

Example 5B

Synthesis of (E)-3-(4-hydroxy-3-methoxyphenyl)-2-propenoic acid 4-(nitrooxy)butyl ester Ferulic acid (97 g, 0.50 mol) was dissolved in methanol (750 ml) and mixed with a solution of potassium hydroxyde (33 g, 0.050 mol) in methanol (250 ml) to give a clear solution at 27° C. The potassium salt of ferulic acid was precipitated by addition of toluene (1250 ml).

The suspension was cooled to 20° C., filtered, and washed with toluene (250 ml) and pentane (2×250 ml). The wet cake was dissolved in DMF (750 ml), and potassium iodide (25 g) and crude 4-Bromo-1-butylnitrate (165 g, 0.83 mol) were added. The reaction mixture was stirred for 16 hours at 20-22° C. The reaction was added with water (750 ml) and the resulting mixture was extracted with t-Butyl-methylether (800 ml+500 ml). The combined extracts were washed with water (750 ml), with 25% sodium chloride aqueous solution (250 ml), dried over sodium sulphate (250 g), filtered, and evaporated at 50° C. (external bath water temperature) under vacuum to give a light brown oil (220 g). Cyclohexane (500 ml) was added, and the mixture was heated to 50° C. to give a two phases system, a colorless upper phase and a dark lower phase. The stirred mixture was cooled to room temperature for 15 hours to give a dark solid cake and a white suspension of fluffy material. The solid was crushed and the suspension was filtered. The cake was washed with cyclohexane (2×50 ml) and dried at 45° C. to provide the desired ester (128.8 g) with 92% purity. Analytically pure product was obtained by crystallization from toluene.

The invention claimed is:

1. A process for preparing a compound of general formula (A)

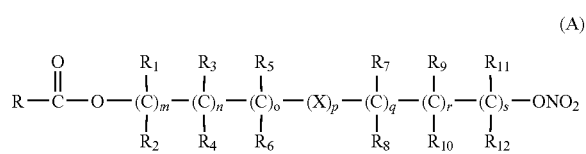

(A)

wherein $R_1$-$R_{12}$ are the same or different and independently are hydrogen, straight or branched $C_1$-$C_6$ alkyl, optionally substituted with aryl;

m, n, o, q, r and s are each independently an integer from 0 to 6, and p is 0 or 1, and X is O, S, SO, $SO_2$, $NR_{13}$ or $PR_{13}$, in which $R_{13}$ is hydrogen, $C_1$-$C_6$ alkyl, or X is selected from the group consisting of:

saturated or unsaturated $C_5$-$C_7$ cycloalkylene, optionally substituted with one or more straight or branched $C_1$-$C_3$ alkyl groups;

arylene, optionally substituted with one or more halogen atoms, straight or branched alkyl groups containing from 1 to 4 carbon atoms, or a straight or branched $C_1$-$C_3$ perfluoroalkyl;

a 5 or 6 member saturated, unsaturated, or aromatic heterocyclic ring selected from

(X1)

(X2)

(X3)

-continued

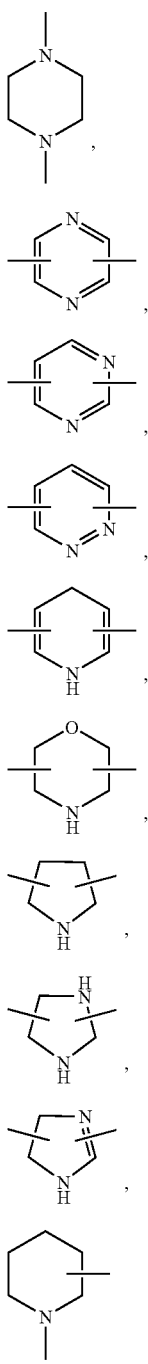

and R is the radical of a pharmacologically active compound selected from the group consisting of:

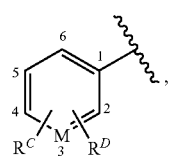

-continued

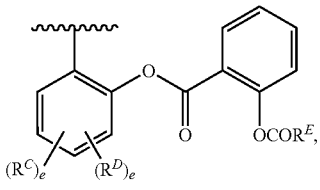

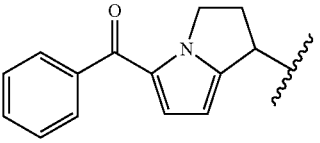

wherein M is a carbon or nitrogen atom;

$R^C$ is selected from: H, OH, $NH_2$, $R^E CONH-$, $R^E COO-$, an heterocyclic residue with 5 or 6 atoms that may be aromatic, saturated or unsaturated, containing one or more heteroatoms selected from oxygen, nitrogen or sulfur, and phenylamino (PhNH—), in which the aromatic ring may be substituted with one or more substituents selected from the group consisting of halogen, straight or branched $C_1$-$C_4$-alkyl and straight or branched perfluoroalkyl;

e is 0 or 1;

$R^E$ is selected from the group consisting of straight or branched $C_1$-$C_5$-alkyl, phenyl substituted with $OCOR^F$, wherein $R^F$ is selected from the group consisting of methyl, ethyl or straight or branched $C_3$-$C_6$-alkyl or phenyl;

$R^D$ is selected from: H, OH, halogen, —$NH_2$, straight or branched $C_1$-$C_6$-alkoxy, perfluoroalkyl having from 1 to 4 carbon atoms and mono or di-$(C_1$-$C_6)$alkylamino; with the proviso that $R^C$ and $R^D$ cannot both be H:

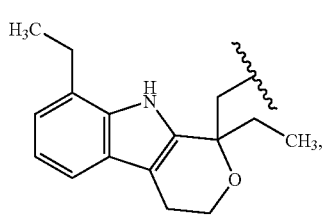

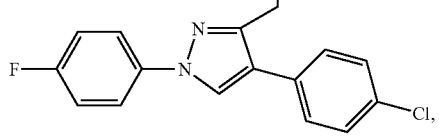

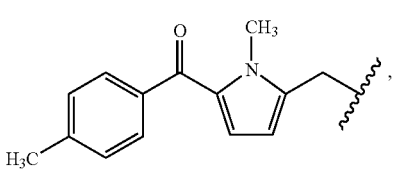

-continued
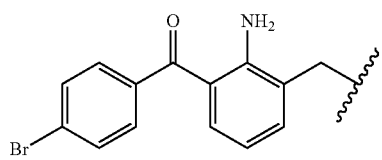
(VII)
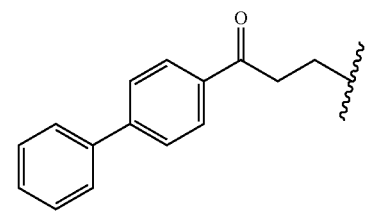
(VIII)
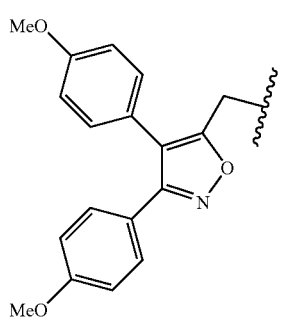
(IX)
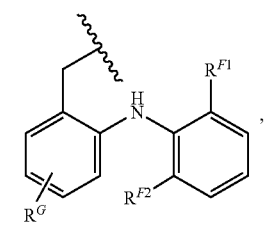
(X)
wherein $R^{F1}$ and $R^{F2}$ are halogens selected from chlorine, fluorine or bromine, $R^G$ is hydrogen, straight or branched $C_1$-$C_6$-alkyl;
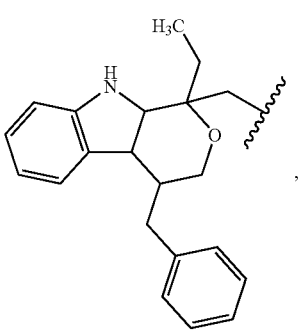
(XI)
-continued
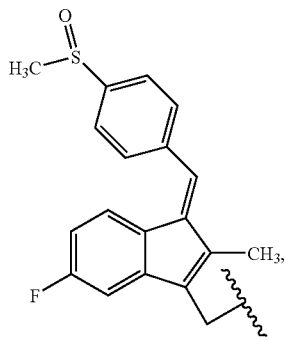
(XII)
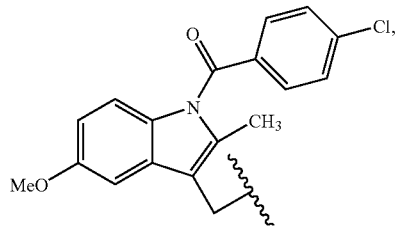
(XIII)
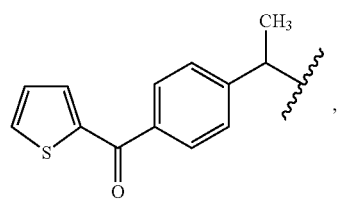
(XIV)
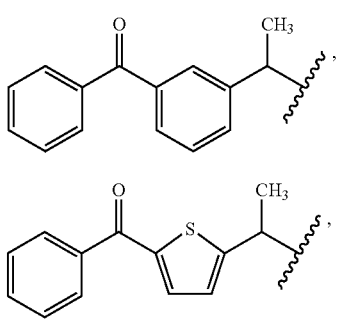
(XV)
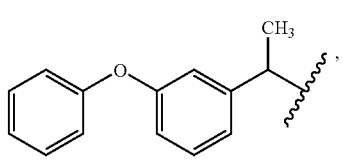
(XVI)
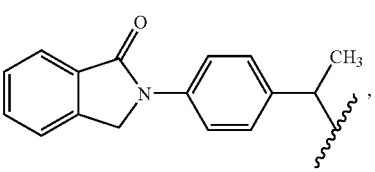
(XVII)
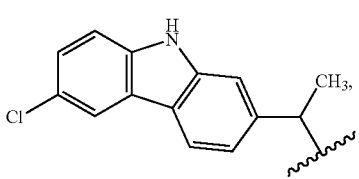
(XVIII)
(XIX)

-continued

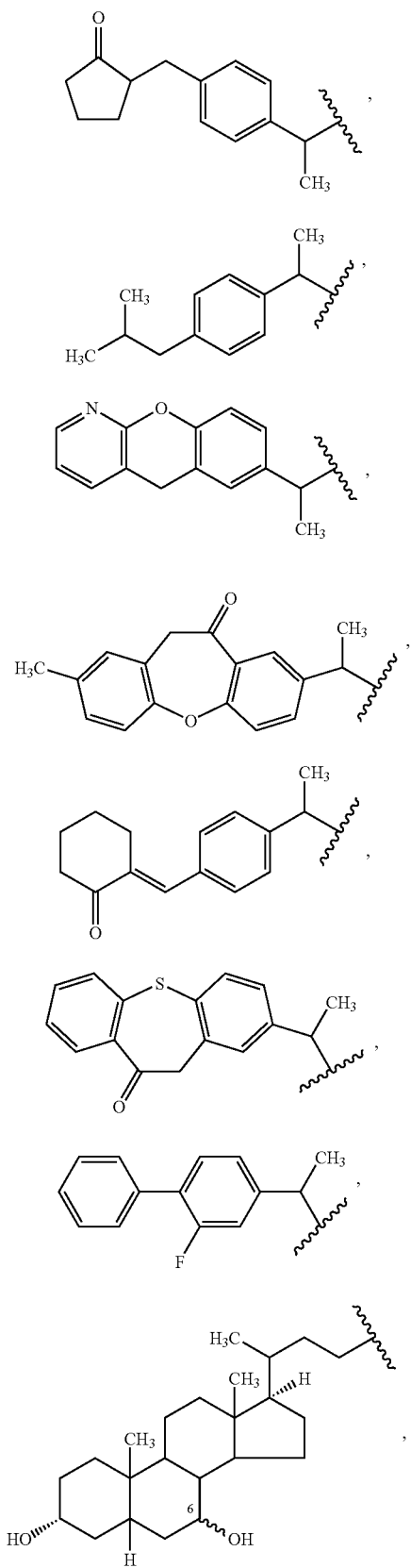

(XXI)
(XXII)
(XXIII)
(XXIV)
(XXV)
(XXVI)
(XXVII)
(XXVIII)

-continued

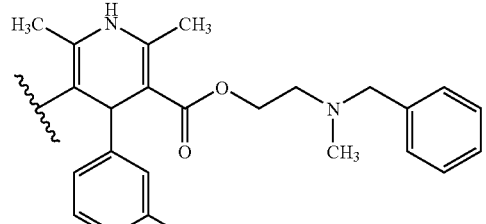

(XXIX)

(XXX)

(XXXI)

wherein the bond at 6 position in formula (XXVIII) may be α or β;

and wherein in all the formulae (I-XXXI) listed above, the wavy line represents the position wherein —COO— group is bound;

said process comprising reacting a compound of formula (B)

R—COOZ  (B)

wherein R is as above defined and Z is hydrogen or a cation selected from Li+, Na+, K+, Ca++, Mg++, tetralkylammonium, tetralkylphosphonium, with a compound of formula (C)

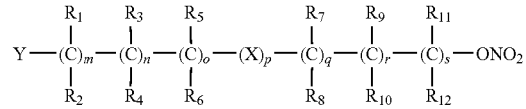

(C)

wherein $R_1$-$R_{12}$ and m, n, o, p, q, r, s are as defined above and

Y is $R_4SO_3$—, in which $R_4$ is a straight or branched $C_1$-$C_6$ alkyl, optionally substituted with one or more halogen atoms, or a $C_1$-$C_6$ alkylaryl.

2. A process for preparing a compound of formula (A) according to claim 1 wherein:

the substituents $R_1$-$R_{12}$ are the same or different and independently are hydrogen or straight or branched $C_1$-$C_3$ alkyl, m, n, o, p, q, r and s are as defined above, X is O, S or

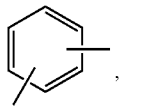 (X1)

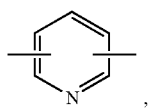 (X2)

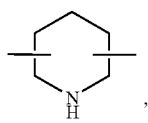 (X3)

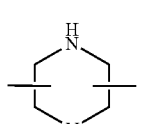 (X4)

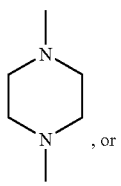 , or (X5)

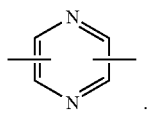 .

3. A process for preparing a compound of formula (A) according to claim 1 wherein $R_1$-$R_4$ and $R_7$-$R_{10}$ are hydrogens; m, n, q, and r are 1; o and s are 0; p is 0 or 1; and X is O or S.

4. A process for preparing a compound of formula (A)

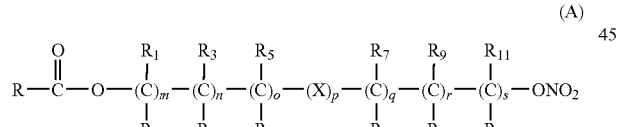 (A)

wherein R is the ferulic acid radical of formula (XXXII):

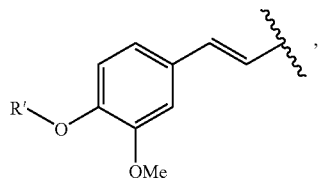 (XXXII)

wherein R' is H, or a group R(CO)—, in which R is as above identified;

and wherein the wavy line represents the position wherein a —COO group is bound;

$R_1$-$R_{12}$ are the same or different and independently are hydrogen, straight or branched $C_1$-$C_6$ alkyl, optionally substituted with aryl;

m, n, o, q, r and s are each independently an integer from 0 to 6, and p is 0 or 1, and X is O, S, SO, $SO_2$, $NR_{13}$ or $PR_{13}$, in which $R_{13}$ is hydrogen, $C_1$-$C_6$ alkyl, or X is selected from the group consisting of:

saturated or unsaturated $C_5$-$C_7$ cycloalkylene, optionally substituted with one or more straight or branched $C_1$-$C_3$ alkyl groups;

arylene, optionally substituted with one or more halogen atoms, straight or branched alkyl groups containing from 1 to 4 carbon atoms, or a straight or branched $C_1$-$C_3$ perfluoroalkyl;

a 5 or 6 member saturated, unsaturated, or aromatic heterocyclic ring selected from

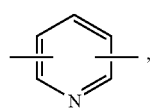 (X1)

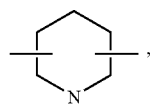 (X2)

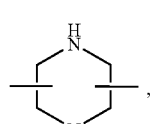 (X3)

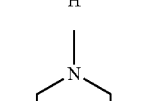 (X4)

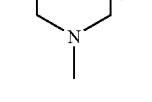 (X5)

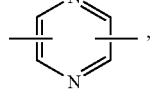 (X6)

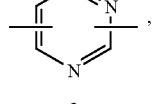 (X7)

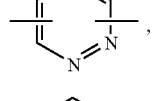 (X8)

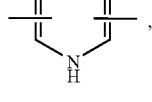 (X9)

-continued

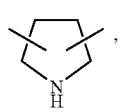 (X10)

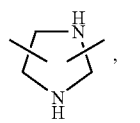 (X11)

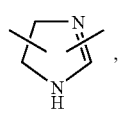 (X12)

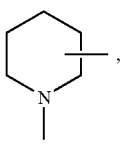 (X13)

said process comprising reacting a compound of formula (B):

R—COOZ        (B)

wherein R is as above defined and Z is hydrogen or a cation selected from Li+, Na+, K+, Ca++, Mg++, tetralkylammonium, tetralkylphosphonium, with a compound of formula (C):

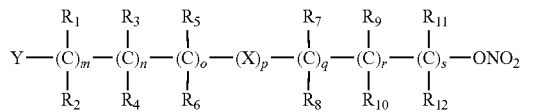 (C)

wherein $R_1$-$R_{12}$ and m, n, o, p, q, r, s are as defined above and

Y is selected from —$BF_4$, —$SbF_6$, $FSO_3$—, $R_A SO_3$—, in which $R_A$ is a straight or branched $C_1$-$C_6$ alkyl, optionally substituted with one or more halogen atoms, or a $C_1$-$C_6$ alkylaryl;

$R_B$COO—, wherein $R_B$ is straight or branched $C_1$-$C_6$ alkyl, aryl, optionally substituted with one or more halogen atoms or $NO_2$ groups, $C_4$-$C_{10}$ heteroaryl and containing one or more heteroatoms, which are the same or different, selected from nitrogen, oxygen sulfur and phosphorus;

aryloxy optionally substituted with one or more halogen atoms or $NO_2$ groups, or heteroaryloxy.

5. A process for preparing a compound of formula (A) according to claim 4, wherein Y is selected from the group consisting of $BF_4$, —$SbF_6$, $FSO_3$—, $CF_3SO_3$—, $C_2F_5SO_3$—, $C_3F_7SO_3$—, $C_4F_9SO_3$—, p-$CH_3C_6H_4SO_3$—.

6. A process for preparing a compound of formula (A) according to claim 1 or 4, wherein the reaction is performed in an organic solvent selected from acetone, tetrahydrofurane, dimethylformamide, N-methylpyrrolidone, sulfolane and acetonitrile.

7. A process for preparing a compound of formula (A) according to claim 1 or 4, wherein the reaction is performed in a biphasic system comprising an aprotic dipolar solvent selected from toluene, chlorobenzene, nitrobenzene, tert-butyl-methylether and a water solution wherein the organic solution contains (C) and the water solution contain an alkaline metal salt of (B), in presence of a phase transfer catalyst.

8. A process for preparing a compound of formula (A) according to claim 1 or 4, wherein the reaction is performed at a temperature ranging from 0° C. to 100° C.

9. A process for preparing a compound of formula (A) according to claim 1 wherein the compounds of formula B and C are reacted at a (B)/(C) molar ratio of 2-0.5.

10. A process for preparing a compound of formula (A) according to claim 4, wherein $R_1$-$R_{12}$ are the same or different and independently are hydrogen or a straight or branched $C_1$-$C_3$ alkyl, m, n, o, p, q, r and s are as defined above, X is O, S or

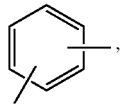 (X1)

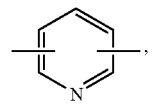 (X2)

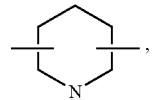 (X3)

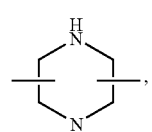 , or (X4)

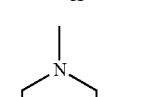 . (X5)

11. A process for preparing a compound of formula (A) according to claim 4, wherein $R_1$-$R_4$ and $R_7$-$R_{10}$ are hydrogens; m, n, q and r are 1; o and s are 0; p is 0 or 1; and X is O or S.

12. A process for preparing a compound of formula (A) according to claim 1, wherein Y is selected from the group consisting of $CF_3SO_3$—, $C_2F_5S_3$—, $C_3F_7SO_3$—, $C_4F_9SO_3$—, and p-$CH_3C_6H_4SO_3$—.

* * * * *